United States Patent
Chatalic et al.

(10) Patent No.: US 11,116,979 B2
(45) Date of Patent: Sep. 14, 2021

(54) ACTIVE IMPLANTABLE MEDICAL NEUROSTIMULATION DEVICE WITH SECTORAL ELECTRODES THAT ARE SWITCHABLE ACCORDING TO VARIOUS CONFIGURATIONS

(71) Applicant: SORIN CRM SAS, Clamart (FR)

(72) Inventors: Guillaume Chatalic, Clamart (FR); Marc LaFlutte, Versailles (FR); Jean-Claude Bierg, Coubron (FR)

(73) Assignee: Sorin CRM SAS, Clamart (FR)

( * ) Notice: Subject to any disclaimer, the term of this patent is extended or adjusted under 35 U.S.C. 154(b) by 289 days.

(21) Appl. No.: 16/071,035

(22) PCT Filed: Jan. 9, 2017

(86) PCT No.: PCT/EP2017/050349
§ 371 (c)(1),
(2) Date: Dec. 20, 2018

(87) PCT Pub. No.: WO2017/125274
PCT Pub. Date: Jul. 27, 2017

(65) Prior Publication Data
US 2019/0111267 A1  Apr. 18, 2019

(30) Foreign Application Priority Data

Jan. 20, 2016 (FR) ...................... 1650446

(51) Int. Cl.
*A61N 1/36* (2006.01)
*A61N 1/05* (2006.01)
*A61N 1/02* (2006.01)

(52) U.S. Cl.
CPC ......... *A61N 1/36157* (2013.01); *A61N 1/025* (2013.01); *A61N 1/0534* (2013.01);
(Continued)

(58) Field of Classification Search
CPC .... A61N 1/025; A61N 1/0534; A61N 1/0556; A61N 1/36053; A61N 1/36057; A61N 1/36157
See application file for complete search history.

(56) References Cited

U.S. PATENT DOCUMENTS 6,516,227 B1 * 2/2003 Meadows .......... A61N 1/36071
  607/46
6,743,066 B1 * 6/2004 Oguchi ..................... H01J 9/02
  445/3

(Continued)

FOREIGN PATENT DOCUMENTS

EP  2 946 806 A1  11/2015

OTHER PUBLICATIONS

International Search Report and Written Opinion on International Application No. PCT/EP2017/050349 dated Mar. 10, 2017. 9 pages.

*Primary Examiner* — Christopher A Flory
(74) *Attorney, Agent, or Firm* — Foley & Lardner LLP

(57) ABSTRACT

A device which includes a generator of electric current pulses and a neurostimulation probe with M sectoral electrodes forming stimulation poles for passing a current between at least one anode and at least one cathode in a predetermined stimulation configuration. The generator includes N current sources and N current sinks, the N sources and the N sinks being defined independently of the M electrodes. A first distribution circuit can indiscriminately and dynamically switch any of the N sources to any of the M electrodes, and a second distribution circuit can indiscriminately and dynamically switch any of the N sinks to any of the M electrodes. The device can thus define a plurality of commutation combinations between sources and/or sinks, providing a single average current in the organ to be stimulated for different respective predetermined pole configurations.

12 Claims, 5 Drawing Sheets

(52) U.S. Cl.
CPC ....... *A61N 1/0556* (2013.01); *A61N 1/36053* (2013.01); *A61N 1/36057* (2013.01)

(56) References Cited

U.S. PATENT DOCUMENTS

| | | | | |
|---|---|---|---|---|
| 6,993,384 B2* | 1/2006 | Bradley | ............... | A61N 1/0551 607/2 |
| 8,121,703 B1* | 2/2012 | Palmer | ............... | A61N 1/36125 607/74 |
| 2003/0139781 A1* | 7/2003 | Bradley | ............... | A61N 1/0551 607/48 |
| 2010/0106219 A1* | 4/2010 | Torgerson | .......... | A61N 1/36125 607/59 |
| 2010/0152817 A1* | 6/2010 | Gillbe | ............... | A61N 1/36021 607/72 |
| 2011/0106213 A1* | 5/2011 | Davis | .................... | G16H 40/63 607/59 |
| 2011/0106215 A1 | 5/2011 | Moffitt | | |
| 2011/0125224 A1* | 5/2011 | Carbunaru | ......... | A61N 1/36071 607/66 |
| 2011/0160810 A1 | 6/2011 | Griffith | | |
| 2012/0277822 A1* | 11/2012 | Trier | .................. | A61N 1/36125 607/46 |
| 2013/0006331 A1* | 1/2013 | Weisgarber | ........ | A61N 1/36185 607/59 |
| 2013/0310894 A1* | 11/2013 | Trier | .................. | A61N 1/36071 607/59 |
| 2014/0100632 A1 | 4/2014 | Rao et al. | | |
| 2015/0320480 A1* | 11/2015 | Cosman, Jr. | ....... | A61B 18/1482 606/34 |
| 2015/0320481 A1* | 11/2015 | Cosman, Jr. | ........... | A61B 34/10 606/35 |
| 2016/0367813 A1* | 12/2016 | Pepin | ................... | A61N 1/0551 |
| 2017/0095667 A1* | 4/2017 | Yakovlev | ............. | A61B 5/4836 |

* cited by examiner

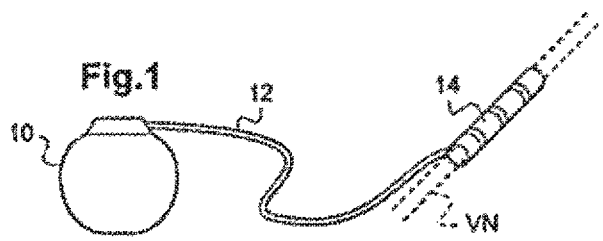
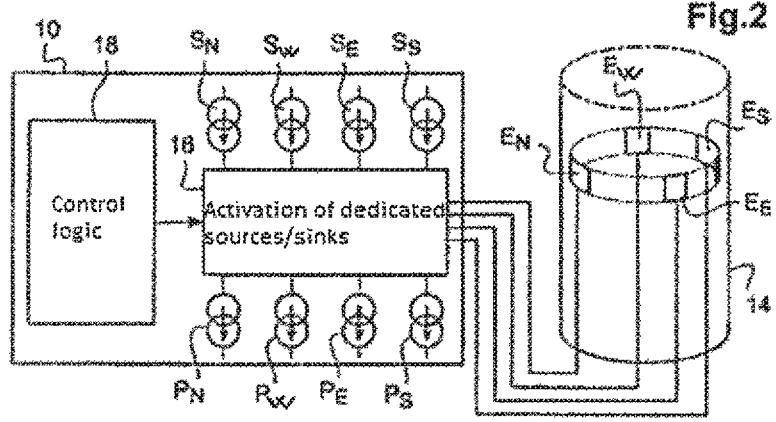
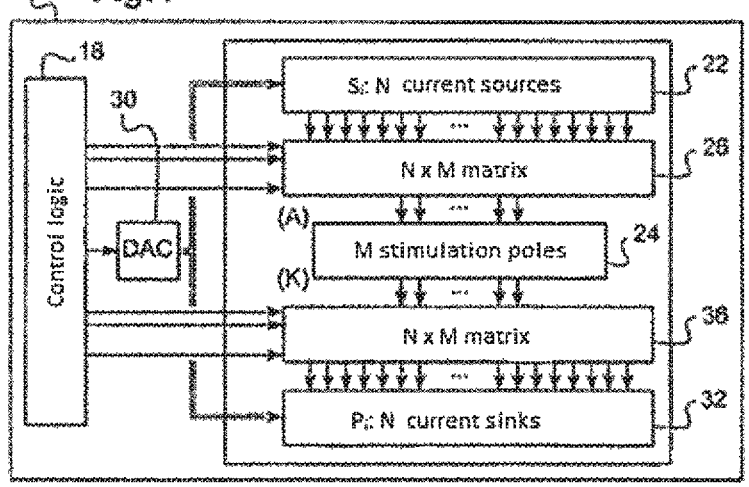

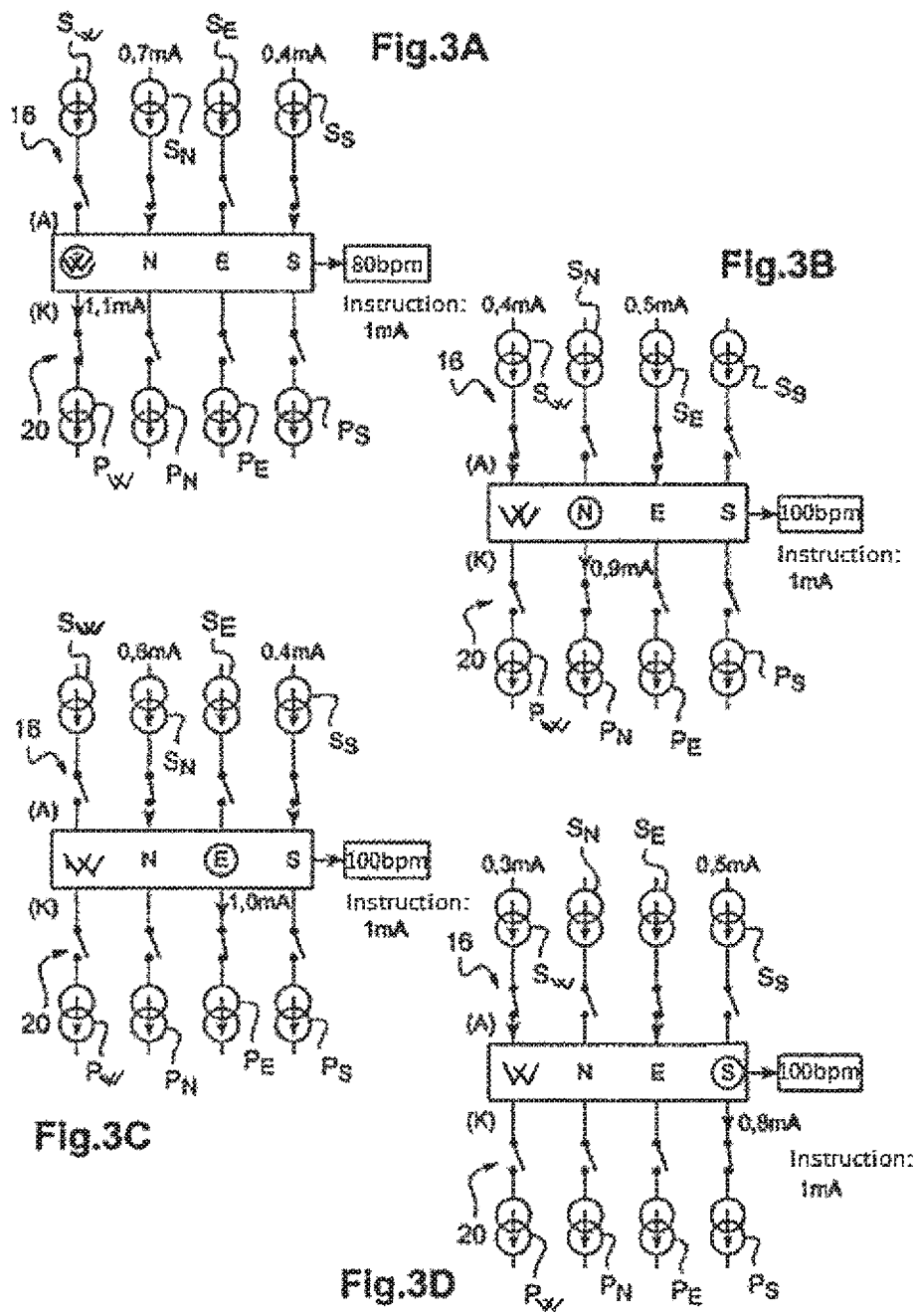

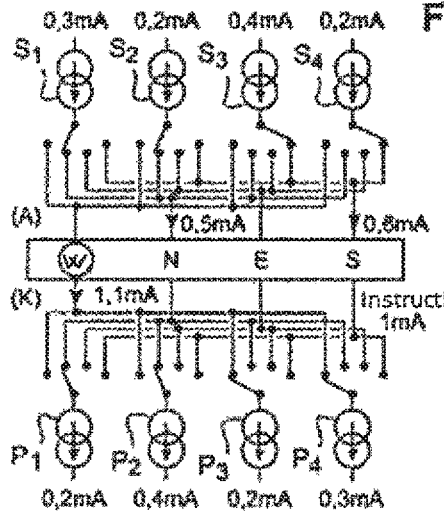
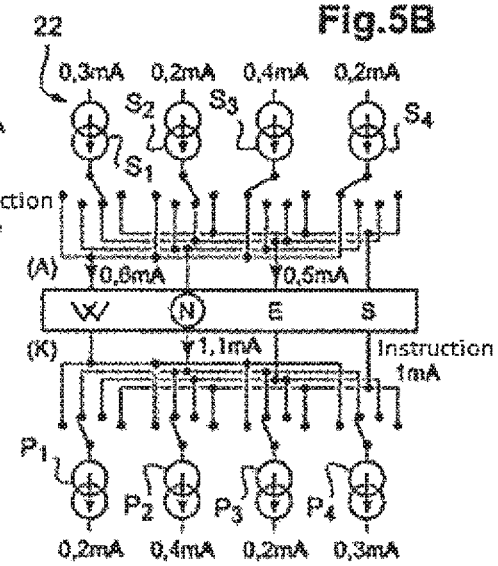

| Pole | Outputted currents (mA) - classic architecture | | | | Outputted currents (mA) - architecture according to the invention | | | |
|---|---|---|---|---|---|---|---|---|
| | $S_W$ | $S_N$ | $S_E$ | $S_S$ | $S_1$ | $S_2$ | $S_3$ | $S_4$ |
| W | -1,1 | +0,7 | — | +0,4 | -1,1 | +0,5 | — | +0,6 |
| N | +0,4 | -0,9 | +0,5 | — | +0,6 | -1,1 | +0,5 | — |
| E | — | +0,6 | -1,0 | +0,4 | — | +0,6 | -1,1 | +0,5 |
| S | +0,3 | — | +0,5 | -0,8 | +0,5 | — | +0,6 | -1,1 |

ACTIVE IMPLANTABLE MEDICAL NEUROSTIMULATION DEVICE WITH SECTORAL ELECTRODES THAT ARE SWITCHABLE ACCORDING TO VARIOUS CONFIGURATIONS

CROSS-REFERENCE TO RELATED PATENT APPLICATIONS

This application is a 371 U.S. National Application of International Application No. PCT/EP2017/050349, filed Jan. 9, 2017, which claims the benefit of and priority to French Patent Application No. 1650446, filed Jan. 20, 2016, which is incorporated herein by reference in its entirety.

BACKGROUND

The invention relates to "active implantable medical devices" as defined by Directive 90/385/EEC of 20 Jun. 1990 from the Council of the European Communities.

It relates more specifically to the implants allowing the delivery of electrical stimulation therapies consisting in applying onto the organs, for therapeutic purposes, a stimulation in the form of repeated electric pulses.

In particular, the electrical stimulation of the nervous system is a therapeutic approach recognized or being evaluated regarding many disorders such as epilepsy, pain, heart failure, sleep apnea, obesity, etc.

Therapy may be delivered in various ways—all included in the scope of the present invention—by means of a neurostimulation probe disposed around, close to or within the targeted organic structure.

The invention relates more specifically to implantable devices allowing to deliver such a nervous system stimulation therapy (hereinafter generally designated "neurostimulation"), including but not limited to a vagus nerve stimulation, so called "VNS" technique (Vagus Nerve Stimulation).

The device comprises a generator delivering electric current pulses, associated with a neurostimulation probe composed in the most common case of a sleeve wound around the nerve. This sleeve is provided with a plurality of electrodes which are applied against the nerve to selectively stimulate some regions by a controlled distribution of the currents applied to the various electrodes. With such a distribution, it consists in targeting the activation of some fibers or axons arranged in the concerned region.

In the following description, we will mainly refer to this mode of delivery of neurostimulation therapy, but it is understood that it isn't restrictive in nature, the invention also being suitable to other types of probes including tubular probes, notably stent shaped tubular probes introduced inside a vessel, for example the aorta, to stimulate some baroreceptor sites having an indirect effect on the nervous system, or the probes implanted directly within the organ, typically a nerve or the brain for a direct stimulation, in situ, of the nervous system.

In the case of the vagus nerve stimulation, it comprises many axons that innervate various organs and muscles of the human body. Some of these axons innervate the organ intended to be subject to therapy (target organ), while others innervate organs that are not affected by the therapy.

Thus, an overall stimulation, undifferentiated, of a nerve may, beyond the desired therapeutic effect, induce adverse effects on other organs or sensory feedbacks. Moreover, to have the desired therapeutic effect via the axon(s) concerned, an undifferentiated excitation of all fibers of a nerve may require a much higher electric current than what is necessary for only the therapeutic effect.

It is therefore important to deliver a spatially selective stimulation of the target organ (typically, but not limited to, a nerve such as the vagus nerve), in order to achieve an effect focused on aimed physiological parameters, by limiting the adverse effects on non-target organs or muscles and limiting the electric current necessary for stimulation.

EP 2 946 806 A1 (Sorin CRM) describes a neurostimulation device comprising a stimulation probe provided for this purpose with electrodes arranged according to several annular areas distributed in the longitudinal direction of the vagus nerve and carried by a sleeve winding it. Each annular area comprises a plurality of sectoral electrodes, that is to say electrodes occupying distinct angular sectors circumferentially distributed over the annular region.

Sectoral electrodes of some annular areas can all be electrically connected together to behave, vis-à-vis the stimulation, in a manner similar to an annular electrode formed of a single piece.

The invention relates to the case, by contrast, where sectoral electrodes are electrodes said "of selectivity", that is to say individually and separately connected to the pulse generator so that each can play either the role of an anode (current entry point into the nerve), the role of a cathode (current output point in the nerve) or be electrically inactive (high impedance behavior).

In a typical example, there are four sectoral electrodes in each annular area and are spaced 90° relative to the next one. By convention, to distinguish them, these four electrodes will be designated "West", "North", "East" and South "(W, N, E and S), the electrodes North and South, or East and West, being arranged in a facing arrangement at 180° from each other while the electrodes West and North, or North and East, etc., are disposed adjacent at 90° from each other.

This number of four sectoral electrodes is however not restrictive, configurations including for example two or eight electrodes, regularly spaced or not, being also possible.

It is thus possible to define, at a same annular area, a plurality of pole configurations of stimulation: for example, in the case of four electrodes, one of the electrodes is connected as a cathode, its two neighboring electrodes are connected as anodes, and the opposite electrode is not connected. This configuration can be transposed by successive rotations of 90°, thus giving four different possible stimulation configurations. Of course, any other connection combination can also be tested.

In general, by "stimulation configuration" is considered any configuration combining the following criteria:
i) the fact that an electrode is or not an active electrode (that is to say, traveled or not by a stimulation current);
ii) the polarity, anode or cathode, of each active electrode (that is to say the direction of the current flowing through this electrode); and
iii) the distribution between the different active electrodes of the current produced by the neurostimulation generator (use of several anodes and/or several cathodes).

Regarding the generator, the conventional structure consists in providing a plurality of current sources and a plurality of current sinks.

The current sources are current generators for injecting current into the nerve at the level of an electrode forming anode, while the current sink are current generators which extract from the nerve, by an electrode forming cathode, the current that had been injected in it by the source(s). A source/sink couple is dedicated to each of the electrodes, so that the sources and sinks are equal in number to that of the electrodes (e.g. four sources and four sinks for a configuration with four sectoral electrodes West-North-East-South). Each source and each sink are static and associated univocally to a specific electrode to which the source or the sink associated therewith can be selectively activated: if the source is activated, the electrode takes the role of a anode, if the sink is activated, the electrode takes the role of cathode and if the source and the sink aren't activated, the electrode will be inactive.

US 2003/0139781 A1 describes such a generator structure, with current sources and sinks selectively switchable to respective electrodes, this structure being described in the context of a multi-electrode probe for stimulation of the spinal cord (SCS, Spinal Cord Stimulation).

By varying the commutation of the current sources and sinks to the various electrodes associated with them, it is possible to test a plurality of predetermined stimulation configurations, in particular for the research of an optimal stimulation configuration that:

maximize the physiological effect produced by the neurostimulation therapy, and minimizes induced undesirable side effects due to nerve stimulation (e.g. triggering coughing).

EP 2 946 806 A1 above-mentioned describes a technique for searching fully automatically such an optimal stimulation configuration depending on the desired physiological effect.

The test of the different stimulation configurations assumes however, so that the achieved physiological effects can be compared, that from a configuration to the other i) the total current flowing through the nerve is the same and that ii) if multiple electrodes are used as anodes or as cathodes, current injection at each cathode and each anode is faithful to a given instruction, which is not necessarily balanced.

But realistically, this is not the case. Indeed, testing various stimulation configurations leads to choose to use current sources that are different of the generator, and these current sources do not deliver identical currents.

Indeed, the current sources (and current sinks as well) are analog microelectronic structures prone to inaccuracies during their manufacturing process: in practice, no manufacturing process ensures an exactly identical geometry for all the transistors on which the microelectronic circuits are based; oxidation, doping, lithography, etc., being never perfectly identical from a transistor to another. This so-called mismatch phenomenon, specific to the analog nature of current sources based on microelectronic circuits, is reflected by the fact that, for a given constant current instruction, different currents generated by the sources are observed, and therefore different currents on the stimulation poles of the organ according to the pole configuration used, because from one configuration to the other it is not the same current sources that are used.

This phenomenon leads to the appearance of a bias on the total current actually delivered to the nerve, which differs from the instructed current used as reference for assessing the produced physiological effect and the comparison of the produced effects between different stimulation configurations.

The introduction of such bias can then lead to poor clinical interpretations of the physiological effects of neurostimulation: in particular, in the presence of this type of bias, it becomes impossible to distinguish the variations of a physiological parameter that are actually resulting from the selection of a pole configuration of different stimulation, to those introduced by mismatches.

Another bias, besides that of the difference between the average current really delivered to the nerve and the instructed current, is that regarding the non-constant nature of the current distribution at the electrodes from a pole configuration to another one. For example, in the case of the use of two anodes with an equivalent instruction, it will not be possible to achieve a 50/50 distribution of currents between the two electrodes. This additional bias may also lead to misinterpretation about the effectiveness of the tested stimulation configuration.

SUMMARY

The object of the invention is to propose a new generator architecture ensuring that for the same input instruction, despite the inevitable mismatches between power generators and between sources and sinks, the current injected into the target organ is the same regardless of the stimulation configuration used, and that the current distribution will be constant regardless of the stimulation configuration used.

The basic idea of the invention is to overcome the conventional architecture wherein a current source and a current sink are dedicated to each stimulation pole (each electrode) according to a one-to-one relation. The invention proposes, in contrast, to separate the current sources from the stimulation poles and to enable a dynamic allocation of each power source of the generator to any stimulation pole, and likewise regarding the current sinks.

It thus becomes particularly possible to conjointly switch several current sources to the same pole, with the result of averaging the current injected by the different sources used: the current flowing through the target organ will then be generally constant regardless of the stimulation configuration selected.

Another benefit of this architecture is the ability to use current sources and sinks in number greater (or less) than that of the electrodes—whereas in a classic architecture, due to the dedicated nature of the sources and sinks, this number should be identical to that of the electrodes.

Thus, by increasing the number of current sources conjointly used to deliver a current at a given electrode, it will be made easier to smooth the mismatches between these different sources by an averaging effect.

More specifically, the invention provides an implantable device for neurostimulation made by controlled injection of electric currents simultaneously at several points of a physiological tissue comprising, in a manner known per se:

a neurostimulation probe adapted to be disposed around, close to or within an organ (VN) comprising at least one arrangement of sectoral electrodes adapted to form stimulation poles with passage of a neurostimulation current between at least one anode and at least one cathode of a predetermined stimulation configuration; and a generator of electric current pulses comprising:
a plurality of current sources;
a plurality of current sinks;
a first distribution structure of currents from said current sources, for selectively coupling at least one of the current sources to an electrode, so that this electrode constitutes an active anode electrode of said predetermined stimulation configuration;
a second distribution structure of currents from said current sinks for selectively coupling at least one of the current sinks to another electrode, so that this other electrode is an active cathode electrode of said predetermined stimulation configuration, According to the invention, the electrode arrangement comprising M electrodes and the generator comprising N current sources and N current sinks, with N=M or N≠M, the N current sources and N current sinks being defined independently of the M electrodes:

the first distribution structure is adapted to operate a coupling indifferently from at least one of the N current sources to any one of the M electrodes;

the second distribution structure is adapted to operate a coupling indifferently from at least one of the N current sinks to any one of the M electrodes; and the generator further comprises control means of the first and second distribution structures adapted to define a combination of couplings from a plurality of current sources and/or from a plurality of current sinks providing a same average neurostimulation current for different respective predetermined stimulation configurations.

According to various advantageous subsidiary characteristics:

said combination of couplings includes a coupling of all current sources, where notably a portion of the N current sources is jointly coupled onto a first anode electrode, and the remaining portion of the N current sources is jointly coupled onto a second anode electrode, different from the first anode electrode;

said combination of couplings include a coupling of all current sinks, where notably a portion of the N current sinks is jointly coupled onto a first cathode electrode, and the remaining portion of the N current sinks is jointly coupled onto a second cathode electrode, different from the first cathode electrode, or else the N current sinks are jointly coupled onto a single cathode electrode;

The control means are preferably multiphasic control means, adapted to cyclically produce a plurality of combinations of couplings for a same stimulation configuration, so as to average the neurostimulation current delivered by the plurality of current sources and the plurality of current sinks.

In the latter case, advantageously:

the control means are adapted to define a combination of couplings of each of the current sources and each of the current sinks successively onto each of the electrodes of the predetermined stimulation configuration;

said plurality of combinations of couplings, produced cyclically for a same stimulation configuration, comprise a circular permutation of the N current sources;

said plurality of combinations of couplings, produced cyclically for a same stimulation configuration, comprise a random permutation of the N current sources;

the control means are means adapted to cyclically produce said plurality of combinations of couplings during successive phases of respective equal durations.

BRIEF DESCRIPTION OF THE DRAWINGS

An example of implementation of the present invention, with reference to the accompanying drawings wherein the same references depicts, from a figure to another, elements that are identical or operatively similar, is described below.

FIG. 1 is an overall view of an implantable neurostimulation device comprising a generator and a stimulation probe of the vagus nerve.

FIG. 2 is a schematic representation of a conventional generator architecture, with dedicated current sources and sinks, associated with a set of respective sectoral electrodes.

FIGS. 3A to 3D respectively illustrate the way to obtain, with a generator architecture according to FIG. 2, four different pole configurations of stimulation, with indication of the current effectively flowing within the different poles of the arrangement of sectorial electrodes.

FIG. 4 is a schematic representation of a generator architecture according to the invention, with current sources and sinks that can be assigned dynamically and undifferentially to any of the stimulation poles.

FIGS. 5A to 5D respectively illustrate how to obtain, with a generator architecture according to the invention, four different pole configurations of stimulation, indicating the currents flowing in the different poles of the arrangement of sectoral electrodes.

DETAILED DESCRIPTION

Figures 6, 8:
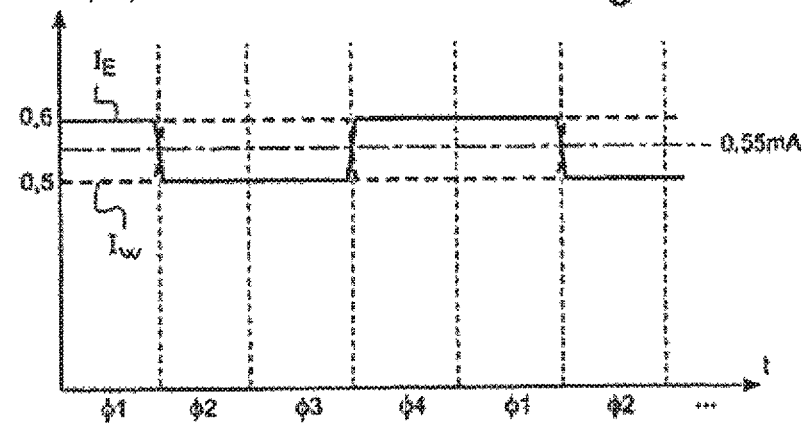
FIG. 6 is a comparison chart showing, for a classic architecture and an architecture according to the invention, input or output currents onto the different active electrodes, depending on the selected stimulation configuration.
FIG. 8 is a timetable showing the sequence of different phases of the technique illustrated in FIGS. 7A to 7D.
Figure 7A:
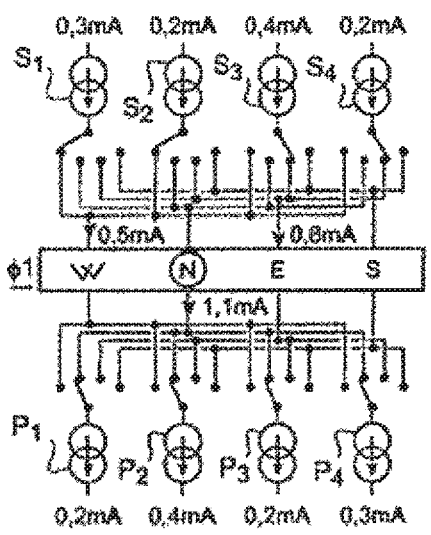
FIGS. 7A to 7D illustrate an improvement of the invention, with cyclic production of a plurality of commutation combinations for a same stimulation configuration.
Figure 7B:
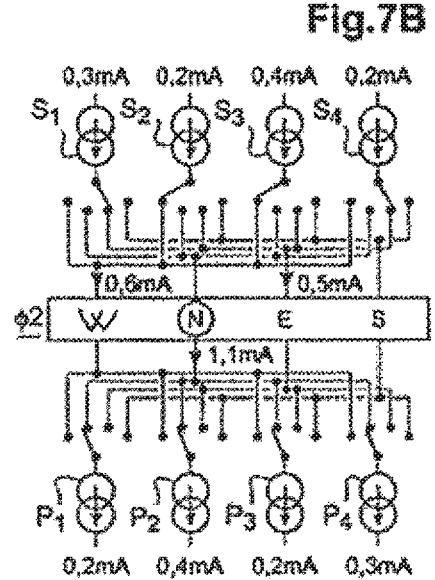
Figure 7C:
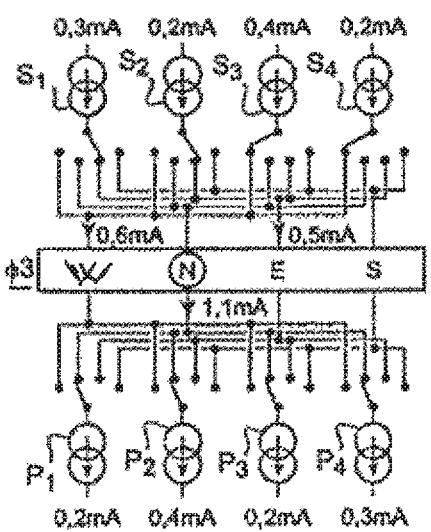
Figure 7D:
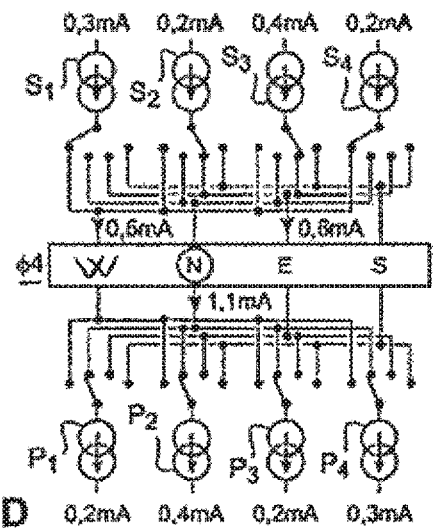

An embodiment of the device of the invention, in the scope (non-restrictive) of a VNS stimulator, that is to say neurostimulation of the vagus nerve, is described below.

Such stimulator comprises a programmable microprocessor provided with circuits for shaping and delivering stimulation pulses to implanted electrodes. It is possible to convey to it, by telemetry, software that will be stored in the memory and executed to implement the functions of the invention that are to be described below. The adaptation of these devices to the implementation of the functions of the invention is within reach of the person skilled in the art, and it will not be described in detail.

Software means are playing a part in the implementation of the invention, with appropriate algorithms executed by a microcontroller or digital signal processor. For the sake of clarity, the various treatments applied will be decomposed and schematized by a number of distinct functional blocks presented in the form of interconnected circuits, but this representation is however only illustrative, these circuits comprising common elements corresponding, in practice, to a plurality of functions globally executed by the same software.

In FIG. 1, reference 10 designates the casing of an implantable generator for vagus nerve stimulation (VNS). This stimulation is delivered by a probe 12 carrying at its distal portion a sleeve 14 carrying an arrangement of electrodes implanted around the vagus nerve VN, in order to selectively stimulate some fibers thereof by injecting electric charges produced by the generator 10 on some electrodes, as discussed in detail below.

FIG. 2 is a block diagram of a conventional architecture of generator 10 connected to a probe sleeve 14.

In FIG. 2, four sectoral electrodes $E_W$, $E_N$, $E_E$ and $E_S$, disposed in an annular arrangement, each electrode occupying a discrete angular sector and being angularly spaced from 90° with respect to the next, are illustrated. By convention, these electrodes each correspond to a stimulation pole respectively designated "West", "North", "East" and "South", but it is understood that this arrangement is in no way restrictive and that it can typically provide between two and eight electrodes regularly spaced or not.

The probe 14 may comprise a plurality of annular arrangements such as the one illustrated in FIG. 2, regularly distributed in the longitudinal direction of the vagus nerve and carried by the same sleeve. The electrodes may be connected together, to behave similarly to an annular electrode of a single piece or—as in the illustrated example corresponding to the case related to the invention—consist of "electrodes of selectivity" individually connected to pulse generator so that each of these electrodes West, North, East and South can play either the role of an anode (a) or the role of a cathode (K) or be unconnected (high impedance behavior).

The generator 10 to which are connected these electrodes comprises four current generators forming sources $S_N$, $S_W$, $S_E$ and $S_S$, equal in number to that of the respective electrodes $E_N$, $E_W$, $E_E$ and $E_S$, to which they may be selectively coupled by a circuit 16 controlled by a digital control logic 18 individually activating each of the dedicated current sources.

Similarly, the generator 10 comprises four current sinks $P_N$, $P_W$, $P_E$ and $P_S$, equal in number to that of the electrodes and selectively coupled thereto via the circuit 16 controlled by the digital control logic 18 individually activating each of the dedicated current sinks.

Thus, according to the state of activation of the circuit 16 as defined by the control logic 18, each $E_i$ electrode will be either be coupled to its respective associated source $S_i$, to act as an anode or to its associated current sink $P_i$, to act as a cathode, or may not be connected, the corresponding electrode thus being inactive.

FIGS. 3A to 3D respectively illustrate the way to obtain, with such a conventional generator architecture, four different pole configurations of stimulation.

In the example illustrated by these figures, are defined four configurations where:
  one of the electrodes is connected as the cathode (e.g. electrode West in FIG. 3A), with a current instruction of 1 mA,
  the diametrically opposed electrode is not connected (electrode East in FIG. 3A), and
  the two neighboring electrodes of the cathode electrode (the electrodes South and North in FIG. 3A) are connected as anodes, with current instructions of 0.5 mA.

The connection as a cathode is operated by connection of the electrode to the corresponding current sink (electrode West to the sink $P_0$ in FIG. 3A) and the connection as an anode to the corresponding current sources (electrodes South and North to the sources $S_S$ and $S_N$ on FIG. 3A).

The stimulation configuration obtained corresponding to the configuration of FIG. 3A will be designated "configuration of selectivity West".

The configuration of FIG. 3B is a "configuration of selectivity North" obtained by a rotation of 90° with respect to the configuration of FIG. 3A. Similarly, the configuration of FIG. 3C is "configuration of selectivity East" obtained by a rotation of 90° with respect to the configuration shown in FIG. 3B and configuration of FIG. 3D is a "configuration of selectivity South" obtained by a rotation of 90° with respect to the configuration of FIG. 3C.

There is thus, in this example, four possible configurations, rotated by 90°, which allow to selectively stimulate different nerve fibers and thereby produce different physiological effects.

It will be understood that other electrode configurations can also be tested, for example configurations with a cathode and an anode which are adjacent, an cathode and an anode which are opposed, a cathode and three anodes, etc., which allows for multiple combinations allowing each time to preferentially stimulate an area of the nerve's section having a specific contour.

Moreover, it is possible not only to play on the position of the anodes to focalize current differently, but also to implement a plurality of cathodes, typically two cathodes, in order to thereby move the annular area and target fibers which would not be located directly under a cathode but rather between two cathodes.

It is also understood that multiplying the number of sectoral electrodes, typically up to eight instead of four, we can define with greater resolution the region of the stimulated nerve, in a privileged way.

The comparisons that can be performed between different pole stimulation configurations obviously assume that the currents injected into the nerve have the same intensity and are distributed in the same way from one configuration to another.

Thus, in the example of FIGS. 3A to 3D, it is assumed that the total current injected into the nerve, corresponding to the current collected on the cathode side is an instructed current of 1 mA, resulting from the injection of 0.5+0.5 mA by the current sources on the anode side.

Effectively, this is not the case, due to the mismatch discussed above resulting from the manufacturing uncertainties of microelectronic structures, from one source to another and between associated source and sink. This phenomenon introduces two biases:
  in absolute value, it is observed that the total current traveling through the nerve is not necessarily equal to the instructed current, and can vary within wide proportions from one configuration to the other: in the example of FIGS. 3A to 3D this current is 1.1 mA for the configuration of selectivity West, 0.9 mA for the configuration of selectivity North, 1.0 mA for the configuration of selectivity East and 0.8 mA for the configuration of selectivity South;
  secondly, the instruction at the anodes (0.5 mA $E_N$ and 0.5 mA for $E_S$ in the case of FIG. 3A) being not exactly met, the current injection is unbalanced: for example, in the configuration of selectivity West, currents of 0.7 mA/0.4 mA, or 64/36 are observed, 0.4 mA/0.5 mA in the configuration of selectivity North, 0.6 mA/0.4 mA in the configuration of selectivity East mA and 0.3 mA/0.5 mA in the configuration of selectivity South.

These biases change significantly, and in a manner which is neither desired nor controllable, the resulting physiological effect, distorting the research of an optimal pole configuration of stimulation.

The search for such optimal configuration is to evaluate, for each possible configuration, the effect on a given physiological parameter: heart rate, cardiac contractility, electroneurogram, etc.

Regarding heart rate, it is known that the application of neurostimulation has among results to reduce this frequency, by modifying the sympathovagal system's balance (negative chronotropic effect of neuro stimulation).

In the examples of FIGS. 3A to 3D, it is shown that for the configuration of selectivity West (FIG. 3A) heart rate is 80 bpm, while for each of the other configurations of selectivity North, East and South (FIGS. 3B, 3C and 3D), this frequency is 100 bpm. In fact, during a first analysis the West configuration of selectivity seems the best, North East and South configurations of selectivity not being able to produce any chronotropic effect.

But this result being impacted by the bias explained above, it is not possible to determine whether the lower heart rate observed:

- is a result of selectivity (choice of a particular pole configuration);
- or a result of mismatch: indeed, in the configuration of FIG. 3A, the injected current (1.1 mA) is higher than that injected into other configurations (respectively 0.9, 1.0 and 0.8 mA). The negative chronotropic effect observed with the configuration of FIG. 3A may thus come partially or totally from the injection of a higher neurostimulation current.

This is the problem that the invention seeks to solve.

To this end, the invention proposes a generator architecture and control of current sources/sinks different from what was just described above with reference to FIGS. 2 and 3A to 3D.

FIG. 4 schematically illustrates the architecture of the generator 10 according to the invention.

On the anode side (upper side of FIG. 4), the generator 10 comprises a set 22 of N current sources Si adapted to be coupled to a set 24 of M stimulation poles (M independent electrodes) via a commutation matrix N×M 26 controlled by the digital control logic 18 via digital links 28. The control logic also runs a digital/analog converter 30 for control of current sources Si.

Similarly, on the cathode side (lower portion of FIG. 4), the generator 10 comprises a set 32 of N current sinks Pi, connected to the M stimulation poles 24 via a commutation matrix N×M 36 controlled by the control logic 18 via digital links 38 and the digital/analog converter 30 to control current sinks Pi.

According to the invention, the current sources/sinks are separate from the stimulation poles, with two consequences:

- the number M of stimulation poles can be equal to the number N of current sources/sinks, or different from the number of current sources/sinks. Advantageously, N>M to increase the balancing effect by averaging the currents conjointly applied to a same pole (as will be described below);
- each of the N current sources and each of the N current sinks can be interchangeably assigned, and in a dynamically manner (that is to say modifiable at any time), to any of the M stimulation poles, that is to say, electrically connected to any of the M electrodes.

The N×M matrices 26 and 36 allow to electrically connect any current source/sink to any electrode, including several sources/sinks to the same electrode. In other words, each of the current generators can be assigned at will, at a given time and in a modifiable manner, to any of the various poles of the stimulation configuration.

FIGS. 5A to 5D respectively illustrate the way to obtain, with a generator architecture according to the invention, four different pole stimulation configurations (being understood that by increasing the number of electrodes it is possible to dispose of more possible configurations of selectivity).

These figures illustrate the respective configurations of selectivity West, North, East, South, with the invention of the generator architecture, compared to the respective counterpart configurations West, North, East, South of FIGS. 3A to 3D implementing a conventional architecture of generators.

In particular, the values of the various currents flowing into the active anode and cathode electrodes are compared.

In the embodiment that is described, for sake of clarity we take N=4 as the number of current sources/sinks, but this choice is in no way restrictive.

In the example shown, the pole defining on the cathode side the configuration of selectivity is jointly connected to all the current sinks, for example in FIG. 5A which describes the configuration of selectivity West, the electrode of the pole West is connected to four current sinks $P_1$, $P_2$, $P_3$ and $P_4$.

On the anode side, the previous pole (counterclockwise), that is to say the pole South, is jointly connected with two of the four sources, in the illustrated example, the sources $S_3$ and $S_4$. The next pole (counterclockwise), that is to say, the pole North is in turn jointly connected with two current sources $S_1$ and $S_2$.

The commutation schemes for the configuration of selectivity North (FIG. 5B), for the configuration of selectivity East (FIG. 5C) and for the configuration of selectivity South (FIG. 5D) are derived from the configuration of FIG. 5A that has just been described by successive rotations of 90°, connecting in the same way the cathode electrode in the set of current sinks and connecting each of the two electrodes which precede and follow to two of the four current sources, respectively.

If the current produced by these different configurations are observed, and their way of distribution as well, we find that:

- the total current injected is the same (1.1 mA) regardless of the configurations of selectivity. This total current injected is actually equal to the sum of the currents delivered by the sources $S_1$, $S_2$, $S_3$ and $S_4$, as follows: 0.3+0.2+0.4+0.2=1.1 mA, because in all configurations the four sources are switched and inject their own current into the nerve;
- secondly, the currents injected into the anode electrodes are always the same: 0.6 mA for the electrode preceding the cathode and 0.5 mA for the electrode following the cathode (in the counterclockwise direction).

In this way, thanks to this architecture, the generator produces a current injected into the nerve that always has the same value (absolute), in this example 1.1 mA, although this value differs from the value of theoretical instruction (1 mA). The current in the nerve will always be the same regardless of the configuration, and the only error that remains is a systematic error, it is not unexpected and dependent of the stimulation configuration.

It should be emphasized that we have a single instruction for all current sources and sinks, the actual current delivered thus being the sum of the currents of the unit sources.

This eliminates the bias that we had with the classic architecture when we modified the stimulation configuration.

Therefore, if we observe a variation of the physiological parameter of a stimulation configuration to another, it means that this variation is related to the different configuration, and not to the variation of the total current injected between different configurations.

FIG. 6 is a comparison table summarizing, for a conventional architecture and an architecture according to the invention, the inputted and outputted currents onto the different active electrodes, depending on the selected stimulation configuration. By convention, a negative value of current corresponds to a current output on the cathode side pole and a positive value to a current flowing into the anode side pole.

It can be observed that:

- on the cathode side, the outputted flow is always the same with the architecture of the invention: 1.1 mA instead of 0.8 to 1.1 mA with the conventional architecture;

the current injected into the preceding anode pole is always 0.5 mA, and the current injected into the following anode pole is always 0.6 mA.

FIGS. 7A to 7D illustrate an improvement of the invention for correcting the differences between the currents injected on the anode side which, although they are the same from one configuration to the other (0.5 and 0.6 mA the example of FIGS. 5A to 5D) are not exactly balanced (the instruction being of 0.5+0.5 mA).

The principle of this improvement consists, over a same stimulation configuration, in controlling dynamically the commutation circuit 26 in alternation with regards to sources, so as to average the actual delivered current at each pole.

It has been seen in the example of FIGS. 5A to 5D that each of the two anode poles was switched to two of the four sources of current. In the case of improvement in question, for a given stimulation configuration, will be operated a permutation of sources switched to the same anode pole during successive phases so that, during each of the phases, always two sources are connected to that pole, but different sources. The permutation can be a circular permutation, or any other permutation. Since each source has the same instruction, we can make random permutations with all sources on one side and all the sinks on the other.

In the example of FIGS. 7A to 7D, the control of the configuration of selectivity North according to this improvement is illustrated.

On the cathode side, the electrode North remains jointly connected to four current sinks $P_1$ to $P_4$.

On the other hand, on the anode side, the commutation configuration of the sources is modified during four successive phases Ø1 to Ø4:

during the stage Ø1, the sources $S_1$ and $S_2$ are connected to the electrode West and the sources $S_3$ and $S_4$ to the electrode East;

during the phase Ø2, the sources $S_2$ and $S_3$ are connected to the electrode West and the sources $S_1$ and $S_4$ are connected to the electrode East;

during phase Ø3, the sources $S_3$ and $S_4$ are connected to the electrode West and the sources S1 and S2 are connected to the electrode East;

during phase Ø4, the sources $S_1$ and $S_4$ are connected to the electrode West and the sources $S_2$ and $S_3$ are connected to the electrode East.

This commutation in four successive phases from Ø1 to Ø4 is executed during the whole duration of neurostimulation.

FIG. 8 is a time chart showing the succession of different phases Ø1 ... Ø4, Ø1, Ø2 ... and the anode currents Iw and IE injected respectively in the electrodes West and East.

The dynamic commutation technique allows to average the current in the electrode West (0.5 mA, then 0.6 mA, then 0.5 mA, etc.) and that in the electrode East (0.6 mA, then 0.5 mA, then 0.6 mA, etc.) to a uniform value of 0.55 mA in each of the two electrodes of the considered pole stimulation configuration, which allows to achieve true symmetry between the two anode electrodes (West and East) surrounding the cathode electrode (North) defining the selected configuration of selectivity.

By repeating the same operation on all the pole configurations, it is ensured that the average current (total electric charge delivered) remains constant regardless of the pole configuration.

To ensure good averaging, it is desirable that the durations of the four phases Ø1 to Ø4 are all equal. The duration of an elementary phase is, ideally, as small as possible to maximize the averaging effect on the duration of neurostimulation if it is achieved as a relatively short pulse. Tangibly, this duration depends on the technological constraints of commutation times of the various switches, etc.

The invention claimed is:

1. An active implantable medical device for neurostimulation, the active implantable medical device configured to provide controlled injection of electric currents simultaneously at several points of a physiological tissue, the active implantable medical device comprising:

a neurostimulation probe adapted to be disposed around, close to or within an organ comprising at least one arrangement of sectoral electrodes adapted to form stimulation poles with passage of a neurostimulation current between at least one anode and at least one cathode of a predetermined stimulation configuration; and a generator comprising a memory having instructions stored thereon and a processor configured to execute the instructions to deliver electric current pulses to the neurostimulation probe, the generator further comprising:

a plurality of current sources;

a plurality of current sinks;

a first distribution structure of currents from said current sources, for selectively coupling at least one of the current sources to an electrode, so that this electrode constitutes an active anode electrode of said predetermined stimulation configuration;

a second distribution structure of currents to said current sinks for selectively coupling at least one of the current sinks to another electrode, so that this other electrode is an active cathode electrode of said predetermined stimulation configuration, wherein the electrode arrangement comprises M electrodes and the generator comprises N current sources and N current sinks, with N=M or N≠M, the N current sources and N current sinks being defined independently of the M electrodes, and wherein the generator is configured such that:

the first distribution structure is adapted to operate a coupling from at least one of the N current sources to any one of the M electrodes;

the second distribution structure is adapted to operate a coupling from at least one of the N current sinks to any one of the M electrodes;

the processor is adapted to define a plurality of combinations of couplings from a plurality of current sources and/or from a plurality of current sinks providing a same average neurostimulation current for different respective predetermined stimulations configurations;

wherein a period of neurostimulation comprises two or more equal length phases, the processor further configured to dynamically switch between the plurality of combinations of couplings at each of the two or more equal length phases.

2. The device of claim 1, wherein said combination of couplings includes a coupling of all current sources.

3. The device of claim 2, wherein a portion of the N current sources is jointly coupled onto a first anode electrode, and the remaining portion of the N current sources is jointly coupled onto a second anode electrode, different from the first anode electrode.

4. The device of claim 1, wherein said combination of couplings includes a coupling of all current sinks.

5. The device of claim 4, wherein a portion of the N current sinks is jointly coupled onto a first cathode electrode, and the remaining portion of the N current sinks is jointly coupled onto a second cathode electrode, different from the first cathode electrode.

6. The device of claim 4, wherein the N current sinks are jointly coupled onto a single cathode electrode.

7. The device of claim 1, wherein the processor is further adapted to execute the instructions to cyclically produce a plurality of combinations of couplings for a same stimulation configuration, so as to average the neurostimulation current delivered by the plurality of current sources and to the plurality of current sinks.

8. The device of claim 7, wherein the processor is further adapted to execute the instructions to define a combination of couplings of each of the current sources and each of the current sinks successively onto each of the electrodes of the predetermined stimulation configuration.

9. The device of claim 7, wherein said plurality of combinations of couplings, produced cyclically for a same stimulation configuration, comprise a circular permutation of the N current sources.

10. The device of claim 7, wherein said plurality of combinations of couplings, produced cyclically for a same stimulation configuration, comprise a random permutation of the N current sources.

11. The device of claim 7, wherein the processor is further adapted to execute the instructions to cyclically produce said plurality of combinations of couplings during successive phases of respective equal durations.

12. The device of claim 1, wherein the at least one arrangement of sectoral electrodes is distributed over an annular region of the neurostimulation probe.

* * * * *